(12) United States Patent
Mortier et al.

(10) Patent No.: US 8,187,323 B2
(45) Date of Patent: May 29, 2012

(54) VALVE TO MYOCARDIUM TENSION MEMBERS DEVICE AND METHOD

(75) Inventors: Todd J. Mortier, Minneapolis, MN (US); Cyril J. Schweich, Jr., St. Paul, MN (US)

(73) Assignee: Edwards Lifesciences, LLC, Irvine, CA (US)

( * ) Notice: Subject to any disclaimer, the term of this patent is extended or adjusted under 35 U.S.C. 154(b) by 205 days.

(21) Appl. No.: 09/981,790

(22) Filed: Oct. 19, 2001

(65) Prior Publication Data

US 2002/0029080 A1    Mar. 7, 2002

Related U.S. Application Data

(63) Continuation of application No. 08/992,316, filed on Dec. 17, 1997, now Pat. No. 6,332,893.

(51) Int. Cl.
*A61F 2/24* (2006.01)

(52) U.S. Cl. ............................................. 623/2.36; 600/37

(58) Field of Classification Search .................... 623/2.1, 623/2.36, 2.37, 3.1, 23.64, 904; 600/37
See application file for complete search history.

(56) References Cited

U.S. PATENT DOCUMENTS

| | | | |
|---|---|---|---|
| 3,019,790 A | 2/1962 | Militana | |
| 3,980,086 A | 9/1976 | Kletschka et al. | |
| 4,192,293 A | 3/1980 | Asrican | |
| 4,261,342 A | 4/1981 | Aranguren Duo | |
| 4,300,564 A | 11/1981 | Furihata | |
| 4,372,293 A | 2/1983 | Vijil-Rosales | |
| 4,409,974 A | 10/1983 | Freedland | |
| 4,536,893 A | 8/1985 | Parravicini | |
| 4,690,134 A | 9/1987 | Snyders | |
| 4,705,040 A | 11/1987 | Mueller et al. | |
| 4,936,857 A | 6/1990 | Kulik | |
| 4,944,753 A | 7/1990 | Burgess et al. | |
| 4,960,424 A | 10/1990 | Grooters | |
| 4,997,431 A | 3/1991 | Isner et al. | |
| 5,104,407 A | 4/1992 | Lam et al. | |
| 5,106,386 A | 4/1992 | Isner et al. | |
| 5,131,905 A | 7/1992 | Grooters | |
| RE34,021 E | 8/1992 | Mueller et al. | |
| 5,169,381 A | 12/1992 | Snyders | |

(Continued)

FOREIGN PATENT DOCUMENTS

DE          36 14 292 C       11/1987

(Continued)

OTHER PUBLICATIONS

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

(Continued)

*Primary Examiner* — David H. Willse
(74) *Attorney, Agent, or Firm* — AnneMarie Kaiser

(57) ABSTRACT

A device for heart valve repair including at least one tension member having a first end and second end. A basal anchor is disposed at the first end of the tension member and a secondary anchor at the second end. The method includes the steps of anchoring the basal anchor proximate a heart valve and anchoring the secondary anchor at a location spaced from the valve such that the chamber geometry is altered to reduce heart wall tension and/or stress on the valve leaflets.

32 Claims, 7 Drawing Sheets

U.S. PATENT DOCUMENTS

| | | | |
|---|---|---|---|
| 5,192,314 A | 3/1993 | Daskalakis | |
| 5,245,102 A | 9/1993 | Zarchy et al. | |
| 5,250,049 A | 10/1993 | Michael | |
| 5,284,488 A | 2/1994 | Sideris | |
| 5,300,087 A | 4/1994 | Knoepfler | |
| 5,360,444 A * | 11/1994 | Kusuhara | 623/2.36 |
| 5,385,528 A | 1/1995 | Wilk | |
| 5,389,096 A | 2/1995 | Aita et al. | |
| 5,417,709 A | 5/1995 | Slater | |
| 5,433,727 A | 7/1995 | Sideris | |
| 5,450,860 A | 9/1995 | O'Connor | |
| 5,452,733 A | 9/1995 | Sterman et al. | |
| 5,458,574 A | 10/1995 | Machold et al. | |
| 5,496,305 A | 3/1996 | Kittrell et al. | |
| 5,509,428 A | 4/1996 | Dunlop | |
| 5,533,958 A | 7/1996 | Wilk | |
| 5,571,215 A | 11/1996 | Sterman et al. | |
| 5,584,803 A | 12/1996 | Stevens et al. | |
| 5,593,424 A | 1/1997 | Northrup, III | |
| 5,665,092 A | 9/1997 | Mangiardi et al. | |
| 5,682,906 A | 11/1997 | Sterman et al. | |
| 5,702,343 A | 12/1997 | Alferness | |
| 5,713,954 A | 2/1998 | Rosenberg et al. | |
| 5,718,725 A | 2/1998 | Sterman et al. | |
| 5,755,783 A | 5/1998 | Stobie et al. | |
| 5,758,663 A | 6/1998 | Wilk et al. | |
| 5,800,334 A | 9/1998 | Wilk | |
| 5,800,528 A | 9/1998 | Lederman et al. | |
| 5,800,531 A | 9/1998 | Cosgrove et al. | |
| 5,807,384 A | 9/1998 | Mueller | |
| 5,814,097 A | 9/1998 | Sterman et al. | |
| 5,840,059 A | 11/1998 | March et al. | |
| 5,849,005 A | 12/1998 | Garrison et al. | |
| 5,855,601 A | 1/1999 | Bessler et al. | |
| 5,855,614 A | 1/1999 | Stevens et al. | |
| 5,865,791 A | 2/1999 | Whayne et al. | |
| 5,928,281 A | 7/1999 | Huynh et al. | |
| 5,957,977 A | 9/1999 | Melvin | |
| 5,961,440 A | 10/1999 | Schweich, Jr. et al. | |
| 5,961,549 A | 10/1999 | Nguyen et al. | |
| 5,971,910 A | 10/1999 | Tsitlik et al. | |
| 5,971,911 A | 10/1999 | Wilk | |
| 5,972,022 A | 10/1999 | Huxel | |
| 5,972,030 A | 10/1999 | Garrison et al. | |
| 5,984,857 A | 11/1999 | Buck et al. | |
| 5,984,917 A | 11/1999 | Fleischman et al. | |
| 5,999,678 A | 12/1999 | Murphy-Chutorian et al. | |
| 6,019,722 A | 2/2000 | Spence et al. | |
| 6,024,756 A | 2/2000 | Huebsch et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,071,303 A | 6/2000 | Laufer | |
| 6,077,214 A | 6/2000 | Mortier et al. | |
| 6,077,218 A | 6/2000 | Alferness | |
| 6,079,414 A | 6/2000 | Roth | |
| 6,086,532 A | 7/2000 | Panescu et al. | |
| 6,102,944 A | 8/2000 | Huynh et al. | |
| 6,117,159 A | 9/2000 | Huebsch et al. | |
| 6,120,520 A | 9/2000 | Saadat et al. | |
| 6,125,852 A | 10/2000 | Stevens et al. | |
| 6,126,590 A | 10/2000 | Alferness | |
| 6,132,438 A | 10/2000 | Fleischman et al. | |
| 6,143,025 A | 11/2000 | Stobie et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,121 A | 12/2000 | Alferness | |
| 6,165,122 A | 12/2000 | Alferness | |
| 6,182,664 B1 | 2/2001 | Cosgrove | |
| 6,197,053 B1 | 3/2001 | Cosgrove et al. | |
| 6,206,004 B1 | 3/2001 | Schmidt et al. | |
| 6,206,820 B1 | 3/2001 | Kazi et al. | |
| 6,217,610 B1 | 4/2001 | Carpentier et al. | |
| 6,221,013 B1 | 4/2001 | Panescu et al. | |
| 6,221,103 B1 | 4/2001 | Melvin | |
| 6,224,540 B1 | 5/2001 | Lederman et al. | |
| 6,238,334 B1 | 5/2001 | Easterbrook, III et al. | |
| 6,245,105 B1 | 6/2001 | Nguyen et al. | |
| 6,258,021 B1 | 7/2001 | Wilk | |
| 6,258,023 B1 | 7/2001 | Rogers et al. | |
| 6,261,222 B1 | 7/2001 | Schweich, Jr. et al. | |
| 6,269,819 B1 | 8/2001 | Oz et al. | |
| 6,283,993 B1 | 9/2001 | Cosgrove et al. | |
| 6,309,370 B1 | 10/2001 | Haim et al. | |
| 6,332,863 B1 | 12/2001 | Schweich, Jr. et al. | |
| 6,332,864 B1 | 12/2001 | Schweich, Jr. et al. | |
| 6,332,893 B1 | 12/2001 | Mortier et al. | |
| 6,338,712 B2 | 1/2002 | Spence et al. | |
| 6,375,608 B1 | 4/2002 | Alferness | |
| 6,379,366 B1 | 4/2002 | Fleischman et al. | |
| 6,406,420 B1 | 6/2002 | McCarthy et al. | |
| 6,416,459 B1 | 7/2002 | Haindl | |
| 6,432,059 B2 | 8/2002 | Hickey | |
| 6,443,949 B2 | 9/2002 | Altman | |
| 6,461,366 B1 | 10/2002 | Seguin | |
| 6,478,729 B1 | 11/2002 | Rogers et al. | |
| 6,508,756 B1 | 1/2003 | Kung et al. | |
| 6,514,194 B2 | 2/2003 | Schweich, Jr. et al. | |
| 6,520,904 B1 | 2/2003 | Melvin | |
| 6,544,180 B1 | 4/2003 | Doten et al. | |
| 6,572,529 B2 | 6/2003 | Wilk | |
| 6,589,160 B2 | 7/2003 | Schweich, Jr. et al. | |
| 6,592,619 B2 | 7/2003 | Melvin | |
| 6,612,278 B2 | 9/2003 | Kampichler | |
| 6,629,921 B1 | 10/2003 | Schweich, Jr. et al. | |
| 6,645,139 B2 | 11/2003 | Haindl | |
| 6,651,671 B1 | 11/2003 | Donlon et al. | |
| 6,673,009 B1 | 1/2004 | Vanden Hoek et al. | |
| 6,676,702 B2 | 1/2004 | Mathis | |
| 6,681,773 B2 | 1/2004 | Murphy et al. | |
| 6,682,474 B2 | 1/2004 | Lau et al. | |
| 6,682,475 B2 | 1/2004 | Cox et al. | |
| 6,682,476 B2 | 1/2004 | Alferness et al. | |
| 6,685,620 B2 | 2/2004 | Gifford, III et al. | |
| 6,685,627 B2 | 2/2004 | Jayaraman | |
| 6,685,646 B2 | 2/2004 | Cespedes et al. | |
| 6,689,048 B2 | 2/2004 | Vanden Hoek et al. | |
| 6,695,768 B1 | 2/2004 | Levine et al. | |
| 6,695,866 B1 | 2/2004 | Kuehn et al. | |
| 6,701,929 B2 | 3/2004 | Hussein | |
| 6,702,732 B1 | 3/2004 | Lau et al. | |
| 6,702,763 B2 | 3/2004 | Murphy et al. | |
| 6,702,826 B2 | 3/2004 | Liddicoat et al. | |
| 6,706,065 B2 | 3/2004 | Langberg et al. | |
| 6,709,456 B2 | 3/2004 | Langberg et al. | |
| 6,712,804 B2 | 3/2004 | Roue et al. | |
| 6,716,158 B2 | 4/2004 | Raman et al. | |
| 6,719,767 B1 | 4/2004 | Kimblad | |
| 6,726,716 B2 | 4/2004 | Marquez | |
| 6,726,717 B2 | 4/2004 | Alfieri et al. | |
| 6,730,016 B1 | 5/2004 | Cox et al. | |
| 6,733,525 B2 | 5/2004 | Yang et al. | |
| 6,740,107 B2 | 5/2004 | Loeb et al. | |
| 6,752,813 B2 | 6/2004 | Goldfarb et al. | |
| 6,755,777 B2 | 6/2004 | Schweich, Jr. et al. | |
| 6,755,779 B2 | 6/2004 | Vanden Hoek et al. | |
| 6,767,362 B2 | 7/2004 | Schreck | |
| 6,769,434 B2 | 8/2004 | Liddicoat et al. | |
| 6,776,754 B1 | 8/2004 | Wilk | |
| 6,790,231 B2 | 9/2004 | Liddicoat et al. | |
| 6,793,673 B2 | 9/2004 | Kowalsky et al. | |
| 6,797,001 B2 | 9/2004 | Mathis et al. | |
| 6,800,090 B2 | 10/2004 | Alferness et al. | |
| 2001/0003986 A1 | 6/2001 | Cosgrove | |
| 2001/0005787 A1 | 6/2001 | Oz et al. | |
| 2001/0009976 A1 | 7/2001 | Panescu et al. | |
| 2001/0021874 A1 | 9/2001 | Carpentier et al. | |
| 2002/0007216 A1 | 1/2002 | Melvin | |
| 2002/0022880 A1 | 2/2002 | Melvin | |
| 2002/0029783 A1 | 3/2002 | Stevens et al. | |
| 2002/0058855 A1 | 5/2002 | Schweich, Jr. et al. | |
| 2002/0065465 A1 | 5/2002 | Panescu et al. | |
| 2002/0091296 A1 | 7/2002 | Alferness | |
| 2002/0111533 A1 | 8/2002 | Melvin | |
| 2002/0111636 A1 | 8/2002 | Fleischman et al. | |
| 2002/0133055 A1 | 9/2002 | Haindl | |

| | | |
|---|---|---|
| 2002/0143250 A1 | 10/2002 | Panescu et al. |
| 2002/0161275 A1 | 10/2002 | Schweich, Jr. et al. |
| 2002/0169359 A1 | 11/2002 | McCarthy et al. |
| 2003/0009081 A1 | 1/2003 | Rogers et al. |
| 2003/0045771 A1 | 3/2003 | Schweich, Jr. et al. |
| 2003/0045896 A1 | 3/2003 | Murphy et al. |
| 2003/0050659 A1 | 3/2003 | Murphy et al. |
| 2003/0105519 A1* | 6/2003 | Fasol et al. ............. 623/2.1 |
| 2003/0149333 A1 | 8/2003 | Alferness |
| 2003/0166992 A1 | 9/2003 | Schweich, Jr. et al. |
| 2003/0171641 A1 | 9/2003 | Schweich, Jr. et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015039 A1 | 1/2004 | Melvin |
| 2004/0015040 A1 | 1/2004 | Melvin |
| 2004/0015041 A1 | 1/2004 | Melvin |
| 2004/0019377 A1 | 1/2004 | Taylor et al. |
| 2004/0019378 A1 | 1/2004 | Hlavka et al. |
| 2004/0024286 A1 | 2/2004 | Melvin |
| 2004/0030382 A1 | 2/2004 | St. Goar et al. |
| 2004/0034271 A1 | 2/2004 | Melvin et al. |
| 2004/0039442 A1 | 2/2004 | St. Goar et al. |
| 2004/0039443 A1 | 2/2004 | Solem et al. |
| 2004/0044365 A1 | 3/2004 | Bachman |
| 2004/0049115 A1 | 3/2004 | Murphy et al. |
| 2004/0049116 A1 | 3/2004 | Murphy et al. |
| 2004/0059180 A1 | 3/2004 | Melvin |
| 2004/0059181 A1 | 3/2004 | Alferness |
| 2004/0059182 A1 | 3/2004 | Alferness |
| 2004/0059187 A1 | 3/2004 | Alferness |
| 2004/0059188 A1 | 3/2004 | Alferness |
| 2004/0059189 A1 | 3/2004 | Alferness |
| 2004/0059351 A1 | 3/2004 | Eigler et al. |
| 2004/0064014 A1 | 4/2004 | Melvin et al. |
| 2004/0073302 A1 | 4/2004 | Rourke et al. |
| 2004/0092962 A1 | 5/2004 | Thornton et al. |
| 2004/0093023 A1 | 5/2004 | Allen et al. |
| 2004/0098116 A1 | 5/2004 | Callas et al. |
| 2004/0102678 A1 | 5/2004 | Haindl |
| 2004/0102679 A1 | 5/2004 | Alferness et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0111101 A1 | 6/2004 | Chin |
| 2004/0122448 A1 | 6/2004 | Levine |
| 2004/0122512 A1 | 6/2004 | Navia et al. |
| 2004/0122513 A1 | 6/2004 | Navia et al. |
| 2004/0127980 A1 | 7/2004 | Kowalsky et al. |
| 2004/0127981 A1 | 7/2004 | Rahdert et al. |
| 2004/0127982 A1 | 7/2004 | Machold et al. |
| 2004/0133062 A1 | 7/2004 | Pai et al. |
| 2004/0133069 A1 | 7/2004 | Shapland et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138526 A1 | 7/2004 | Guenst |
| 2004/0138744 A1 | 7/2004 | Lashinski et al. |
| 2004/0143323 A1 | 7/2004 | Chawla |
| 2004/0148019 A1 | 7/2004 | Vidlund et al. |
| 2004/0148020 A1 | 7/2004 | Vidlund et al. |
| 2004/0152947 A1 | 8/2004 | Schroeder et al. |
| 2004/0158123 A1 | 8/2004 | Jayaraman |
| 2004/0158321 A1 | 8/2004 | Reuter |
| 2004/0162610 A1 | 8/2004 | Liska et al. |
| 2004/0167374 A1 | 8/2004 | Schweich et al. |
| 2004/0167539 A1 | 8/2004 | Kuehn et al. |
| 2004/0171907 A1 | 9/2004 | Alferness et al. |
| 2004/0171908 A1 | 9/2004 | Alferness et al. |
| 2004/0171909 A1 | 9/2004 | Alferness |
| 2004/0172046 A1 | 9/2004 | Hlavka et al. |
| 2004/0176678 A1 | 9/2004 | Murphy et al. |
| 2004/0176679 A1 | 9/2004 | Murphy et al. |
| 2004/0176840 A1 | 9/2004 | Langberg et al. |
| 2004/0181121 A1 | 9/2004 | Alferness et al. |
| 2004/0181122 A1 | 9/2004 | Alferness et al. |
| 2004/0181123 A1 | 9/2004 | Alferness et al. |
| 2004/0181124 A1 | 9/2004 | Alferness |
| 2004/0181125 A1 | 9/2004 | Alferness et al. |
| 2004/0181126 A1 | 9/2004 | Buckberg et al. |
| 2004/0181238 A1 | 9/2004 | Zarbatany et al. |
| 2004/0186342 A1 | 9/2004 | Vanden Hock et al. |
| 2004/0186566 A1 | 9/2004 | Hindrichs et al. |
| 2004/0193191 A1 | 9/2004 | Starksen et al. |
| 2004/0193260 A1 | 9/2004 | Alferness et al. |
| 2004/0243229 A1 | 12/2004 | Vidlund et al. |

FOREIGN PATENT DOCUMENTS

| | | |
|---|---|---|
| DE | 36 14 292 C1 | 11/1987 |
| DE | 42 34 127 A1 | 5/1994 |
| DE | 42 34 127 A1 | 5/1994 |
| DE | 296 19 294 U | 7/1997 |
| DE | 298 24 017 U1 | 6/2000 |
| EP | 0 583 012 | 2/1994 |
| EP | 0 820 729 A1 | 1/1998 |
| WO | 91/19465 | 12/1991 |
| WO | 95/06447 | 3/1995 |
| WO | 95/16476 | 6/1995 |
| WO | WO 95/16407 * | 6/1995 |
| WO | 96/04852 | 2/1996 |
| WO | WO 96/04852 | 2/1996 |
| WO | 96/40356 | 12/1996 |
| WO | WO 97/14286 | 4/1997 |
| WO | 97/24082 | 7/1997 |
| WO | 97/24083 | 7/1997 |
| WO | 97/24101 | 7/1997 |
| WO | WO 97/24101 | 7/1997 |
| WO | 98/03213 | 1/1998 |
| WO | 98/14136 | 4/1998 |
| WO | WO 98/17347 | 4/1998 |
| WO | 98/18393 | 5/1998 |
| WO | WO 98/18393 | 5/1998 |
| WO | 98/26738 | 6/1998 |
| WO | 98/32382 | 7/1998 |
| WO | WO 98/29041 | 7/1998 |
| WO | WO 98/58598 | 12/1998 |
| WO | 99/00059 | 1/1999 |
| WO | 99/11201 | 3/1999 |
| WO | 99/13777 | 3/1999 |
| WO | WO 99/11201 | 3/1999 |
| WO | WO 99/16350 | 4/1999 |
| WO | WO 99/22784 | 5/1999 |
| WO | WO 99/30647 | 6/1999 |
| WO | 99/44534 | 9/1999 |

OTHER PUBLICATIONS

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso-Lej, M.D., "Adjustable Annuloplasty for Tricuspid Insufficiency" *The Annals of Thoracic Surgery*, vol. 46, No. 3, Sep. 1988, 2 pages.

A. Carpentier et al., "Myocardial Substitution with a Stimulated Skeletal Muscle: First Successful Clincial Case", Letter to the Editor, p. 1267, Sep. 25, 1996.

C. David Ianuzzo et al.,, "Preservation of the Latissimus Dorsi Muscle During Cardiomyoplasty Surgery", J. Card. Surg., 1996:11:99-108.

C. David Ianuzzo et al., "Preconditioning of Skeletal Muscle: Application to Dynamic Cardiomyoplasty," Invited Commentary, *J. Card. Surg.*, 1996:11:109-110.

J.C. Chachques et al., "Latissimus Dorsi Dynamic Cardiomyoplasty," *Ann. Thorac. Surg.*, 1989:47:600-604.

L. Moreira et al., "Latissimus Dorsi Cardiomyoplasty in the Treatment of Patients with Dilated Cardiomyopathy," Supplement IV Circulation, Sep. 25, 1996, 7 pgs.

C. Lucas et al., "Long-Term Follow-Up (12 to 35 Weeks) After Dynamic Cardiomyoplasty," *JACC*, vol. 22, No. 3, Sep. 1993:758-67.

R. Batista et al., "Partial Left Ventriculectomy to Improve Left Ventricular Function in End-Stage Heart Disease," *J. Card. Surg.*, 1996:11:96-98.

"Congestive Heart Failure in the United States: A New Epidemic" Data Fact Sheet, National Heart, Lung, and Blood Institute, National Institutes of Health, Dec. 9, 1996, pp. 1-6.

R. Kormos et al., "Experience with Univentricular Support in Mortally III Cardiac Transplant Candidates," *Ann. Thorac. Surg.*, 1990:49:261-71.

R. Wampler et al., "Treatment of Cardiogenic Shock with the Hemopump Left Ventricular Assist Device," *Ann. Thorac. Surg.*, 1991:52:506-13.

P. McCarthy et al., "Clinical Experience with the Novacor Ventricular Assist System," *J. Thorac. Cardiovasc. Surg.*, 1991:102-578-87.

C. Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.

S. Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.

G. Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.

G. Bearnson et al., "Development of a Prototype Magnetically Suspended Rotor Ventricular Assist Device," *ASAIO Journal*, 1996, pp. 275-280.

N. Sakakibara et al., "A Muscle Powered Cardiac Assist Device for Right Ventricular Support: Total Assist or Partial Assist?," *Trans. Am.Soc. Artif. Intern. Organs*, vol. XXXVI, 1990, pp. 372-375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, "ABIOMED's Temporary Artificial Heart System Reaches 200 U.S. Medical Center Milestone," 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED Wins NIH Grant to Develop Calcification-Resistant Plastic Heart Valve," 1 page.

Press Release dated Aug. 25, 1995, "ABIOMED Wins Research Grant from NIH to Develop Suturing Instrument for Abdominal Surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS-5000 in More Than 100 U.S. Medical Centers," 1 page.

"Reversible Cardiomyopathy," *Thoratec's Heartbeat*, vol. 10.2, Aug. 1996, 2 pages.

C. Tsai et al., "Surface Modifying Additives for Improved Device-Blood Compatibility," *ASAIO Journal*, 1994, pp. 619-624.

D. Farrar et al., "A New Skeletal Muscle Linear-Pull Energy Convertor as a Power Source for Prosthetic Support Devices," *The Journal of Heart & Lung Transplantation*, vol. 11, No. 5, Sep. 1992, pp. 341-349.

Brochure entitled "Thoratec Ventricular Assist Device System—Because Heart Patients Come in All Sizes," date even with or prior to Jan. 2, 1997, 3 pages, Press Release dated Oct. 3, 1994, "Heartmate System Becomes First Implantable Cardiac-Assist Device to be Approved for Commercial Sale in the U.S.," 1 page.

E. Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Bach et al., "Early Improvement in Congestive Heart Failure after Correction of Secondary Mitral Regurgitation in End-Stage Cardiomyopathy," *American Heart Journal*, Jun. 1995, pp. 1165-1170.

Schuler et al., "Temporal Response of Left Ventricular Performance to Mitral Valve Surgery," vol. 59, No. 6, Jun. 1979, pp. 1218-1231.

Huikuri, "Effect of Mitral Valve Replacement on Left Ventricular Function in Mitral Regurgitation," *Br. Heart J.*, vol. 49, 1983, pp. 328-333.

Pitarys II et al., "Long-Term Effects of Excision of the Mitral Apparatus on Global and Regional Ventricular Function in Humans," *JACC*, vol. 15, No. 3, Mar. 1, 1990, pp. 557-563.

Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146.

Boyd et al., "Tricuspid Annuloplasty Five and one-half years' experience with 78 patients," *The Annals of thoracic Surgery*, vol. 68, No. 3, Sep. 1974, 8 pages.

Kurlansky et al., "Adjustable Annuloplasty for Tricuspid Insufficiency", Ann. Thorac. Surgery, vol. 44, No. 4, Oct. 1987, 3 pages.

Edie, M.D., "Surgical repair of single ventricle," The Journal of Thoracic and Cardiovascular Surgery, vol. 66, No. 3, Sep. 1973, pp. 350-360.

McGoon, M.D. et al., "Correctionof the univentricular heart having two atrioventricular valves," The Journal of Thoracic and Cardiovascular Surgery, vol. 74, No. 2, Aug. 1977, pp. 218-226.

Lev, M.D. et al., "Single (Primitive) Ventricle," Circulation, vol. 39, May 1969, pp. 577-591.

Westaby with Bosher, "Landmarks in Cardiac Surgery," 1997, pp. 198-199.

Shumacker, "Cardiac Aneurysms," The Evolution of Cardiac Surgery, 1992, pp. 159-165.

Feldt, M.D., "Current status of the septation procedure for univentricular hearet," The Journal of Thoracic and Cardiovascular Surgery, vol. 82, No. 82, No. 1, Jul. 1981, pp. 93-97.

Doty, M.D., "Septation of the univentricular heart," The Journal of Thoracic and Cardiovascular Surgery, vol. 78, No. 3, Sep. 1979, pp. 423-430.

Savage, M.D., "Repair of left ventricular aneurysm," The Journal of Thoracic and Cardiovascular surgery, vol. 104, No. 3, Sep. 1992, pp. 752-762.

Cox, "Left Ventricular Aneurysms: Pathophysiologic Observations and Standard Resection," Seminars in Thoracic and Cardiovascular Surgery, vo.l 9, No. 2, Apr. 1997, pp. 113-122.

Melvin, "Ventricular Radius Reduction Without Resection: A Computational Analysis," ASAIO Journal, 45:160-165, 1999.

Batista, MD et al., "Partial Left Ventriculectomy to Treat End-Stage Heart Disease", *Ann. Thorac. Surg.*, 64:634-8, 1997.

Kay et al., "Surgical Treatment of Mitral Insufficiency", *The Journal of Thoracic Surgery*, 29: 618-620, 1955.

Harken et al., "The Surgical Correction of Mitral Insufficiency", *The Journal of Thoracic Surgery*, 28:604-627, 1954.

Bailey et al., "Closed Intracardiac Tactile Surgery", *Diseases of the Chest*, XXII:1-24, Jul. 1952.

Sakakibara, "A Surgical Approach to the Correction of Mitral Insufficiency", *Annals of Surgery*, 142:196-203, 1955.

Glenn et al., "The Surgical Treatment of Mitral Insufficiency: The Fate of a Vascularized Transchamber Intracardiac Graft", Annals of Surgery, 141:510-518, Apr. 1955.

Kay et al., "Surgical Treatment of Mitral Insufficiency", *Surgery*, 37:697-706, May 1955.

Bailey et al."The Surgical Correction of Mitral Insufficiency by the Use of Pericardial Grafts", *The Journal of Thoracic Surgery*, 28:551-603, Dec. 1954.

Harken et al., "The Surgical Correction of Mitral Insufficiency", Surgical Forum, 4:4-7, 1953.

Shumacker, Jr., "Attempts to Control Mitral Regurgitation", *The Evolution of Cardiac Surgery*, 203-210, 1992.

US 6,197,052, 03/2001, Cosgrove et al. (withdrawn)

* cited by examiner

__US 8,187,323 B2__

VALVE TO MYOCARDIUM TENSION MEMBERS DEVICE AND METHOD

RELATED APPLICATIONS

This application claims priority under 35 U.S.C. §120 as a continuation of U.S. Ser. No. 08/992,316, filed Dec. 17, 1997, now issued as U.S. Pat. No. 6,332,893.

BACKGROUND OF THE INVENTION

The present invention pertains generally to the field of heart valve repair. More specifically, the present invention pertains to a device and method for the reduction of myocardial wall tension and the repair of mitral valve insufficiency.

Dilated cardiomyopathy is often accompanied by mitral valve insufficiency. There are several reasons for the presence of mitral valve insufficiency associated with a dilated heart. First, chamber dilation and associated high wall stresses increase the diameter of the mitral valve annulus. Additionally, as the heart dilates, the positioning of the papillary muscles is altered. Papillary muscles and chordae in a dilated heart will have moved both radially away and down from the mitral valve. This rearrangement of the vascular apparatus and enlargement of the annulus prevent the valve from closing properly.

Currently mitral valve insufficiency is treated by either repairing or replacing the valve. Surgical procedures used to repair the valve including ring posterior annuloplasty which consists of sewing a C or D-shaped ring around the posterior leaflet of the mitral valve and drawing in the annulus, reducing its previously enlarged diameter. Another method is to approximate the anterior and posterior mitral leaflets (Alfieri repair) by placing one suture through the center of both leaflets. This gives the valve a figure 8-shaped appearance when the valve is opened. When the mitral valve is replaced, the original leaflets are removed and the chordae are cut. An artificial valve consists of mechanical or tissue leaflets suspended on struts attached to a metal stent, and is sutured into place on the mitral annulus.

It has been argued that valve repair is preferable to valve replacement if the leaflet-chordae-papillary connections can be maintained. Heart wall stress will increase if the chordae are cut during valve replacement. It has been shown that by severing the chordae there can be 30 percent (30%) reduction in chamber function. Mitral valve replacement has high mortality in very sick, chronic heart failure patients.

SUMMARY OF THE INVENTION

The present invention pertains to a device and method for mitral valve repair. The mitral valve is generally defined as its leaflets or cusps, but in reality, it actually consists of the entire left ventricle chamber. By creating an improved chamber geometry, both chamber and valve function will be improved. The device of the present invention and method for valve repair/replacement can include treatment for chronic heart failure by reducing left ventricular wall tension.

In one embodiment of the present invention, the valve repair device includes an elongate tension member having a first end and second end. The basal anchor is disposed at the first end and the secondary anchor is disposed at the second end.

The basal anchor could include a pad and annuloplasty ring or the like. Alternately an artificial heart valve could serve as the basal anchor.

Tension members can be substantially rigid or substantially flexible. The secondary anchor can include a hook-shaped papillary muscle tissue loop, screw-shaped tissue anchor or transmural anchor pad.

The method of the present invention providing a tension member having a first end and a second end. The tension member has a basal anchor at the first end and a secondary anchor at the second end. The basal anchor is anchored proximate to the valve such that the tension member is disposed in the chamber. The secondary anchor is anchored to a portion of the heart spaced from the basal anchor such that the tension member is under tension and the geometry of the chamber has been altered by placement of the tension member.

The basal anchor can include an artificial heart valve, annuloplasty ring or the like. The secondary anchor can be anchored to a papillary muscle or transmurally anchored.

More than one tension member can be used. Additionally, a transverse tension member can be placed across the chamber generally perpendicular to the other tension members to further alter the geometry of the heart, reducing wall stress and improving chamber performance.

DETAILED DESCRIPTION OF THE INVENTION

Figure 1:
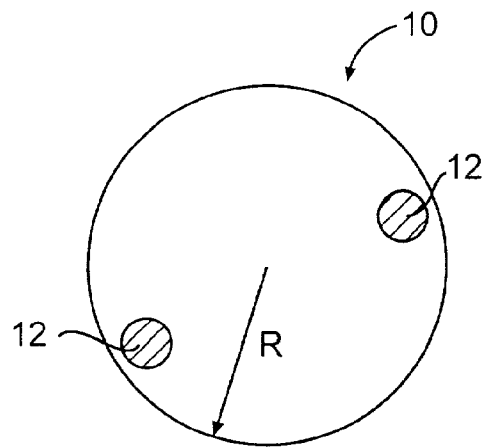
FIG. 1 is a transverse cross section of the left ventricle of a human heart taken from FIG. 2.
Figure 2:
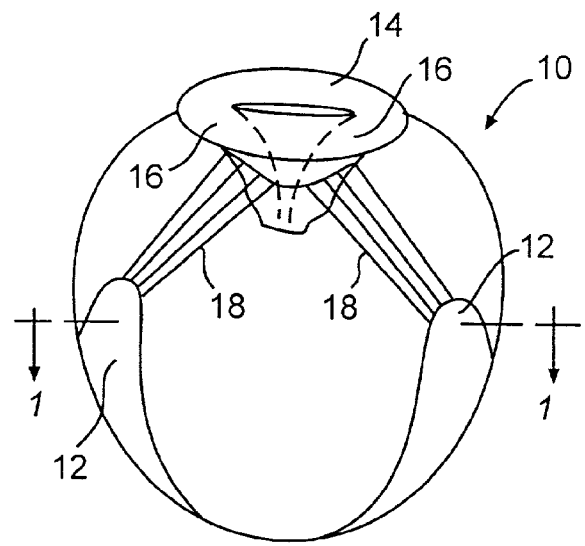
FIG. 2 is a vertical cross section of the left ventricle of a human heart.

Referring now the drawings wherein like reference numerals refer to like elements throughout the several views, FIG. 1 shows a transverse cross section of the left ventricle 10 of a failing heart taken from FIG. 2. The papillary muscles 12 are shown in cross section. FIG. 2 is a vertical cross section of human heart 10. A mitral valve is disposed near the top of left ventricle 10. Mitral valve 14 includes two leaflets or cusps 16. Chordae 18 extend between leaflets 16 and papillary muscles 12.

Figure 3:
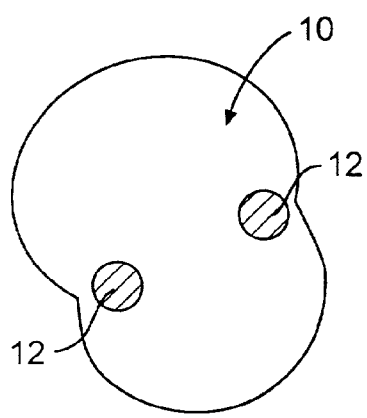
FIG. 3 is a modified, transverse, cross section of the left ventricle of a human heart taken from FIG. 4.
Figure 4:
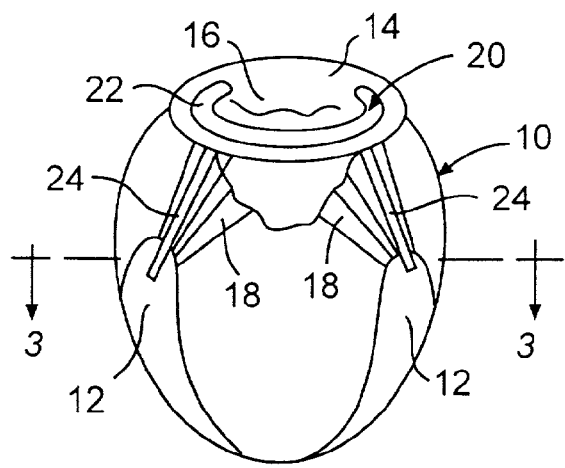
FIG. 4 is modified, vertical cross section of a human heart, modified by a device in accordance with the present invention.

FIG. 3 is a cross section of heart 10 modified from that shown in FIG. 1 by placement of valve repair device 20 in accordance with the present invention as shown in FIG. 4. FIG. 4 is a vertical cross section of left ventricle 10 with geometry modified by device 20. In this embodiment of the invention, device 20 includes a basal anchor 22 such as an annuloplasty or suture ring sewn proximate the annulus of valve 14. Extending from basal anchor 22 are elongate tension members 24. Each have a first end connected to basal anchor 22 and a second end anchored to papillary muscles 12 or the heart wall.

As can be seen in FIGS. 3 and 4, both the transverse radius and vertical dimension of left ventricle 10 has been reduced in comparison to that of FIGS. 1 and 2 by drawing papillary muscles 12 toward valve 14 with tension members 24. This change in geometry reduces heart wall stress and consequently increasing chamber function. Valve function is also improved as explained in more detail by reference to FIGS. 5 and 6.

Figure 5:
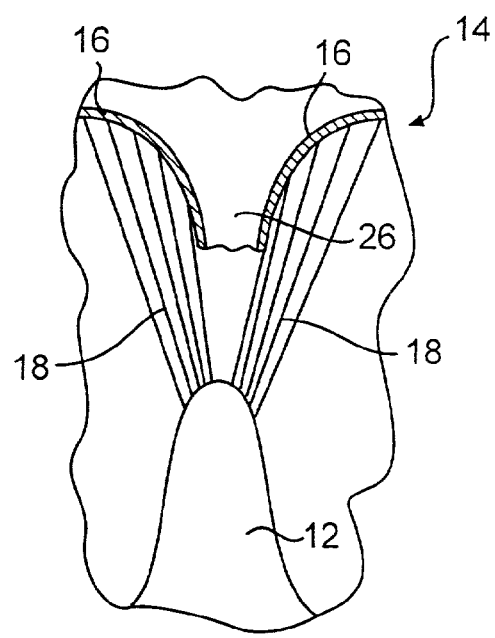
FIG. 5 is a cross section of an insufficient mitral valve of a left ventricle of a human heart.

FIG. 5 is a generally vertical cross section of an insufficient mitral valve of a heart suffering from chronic heart failure. In this case as the failing heart has dilated, papillary muscle 12 has been drawn away from mitral valve 14. The chordae connections between papillary muscles 12 and valve 14 in turn draws leaflets 16 apart such that during the normal cardiac cycle, leaflets 16 may not completely close. Thus, an opening 26 is left between leaflets 16 throughout the cardiac cycle. Opening 26 will allow blood to leak, reducing chamber efficiency.

Figure 6:
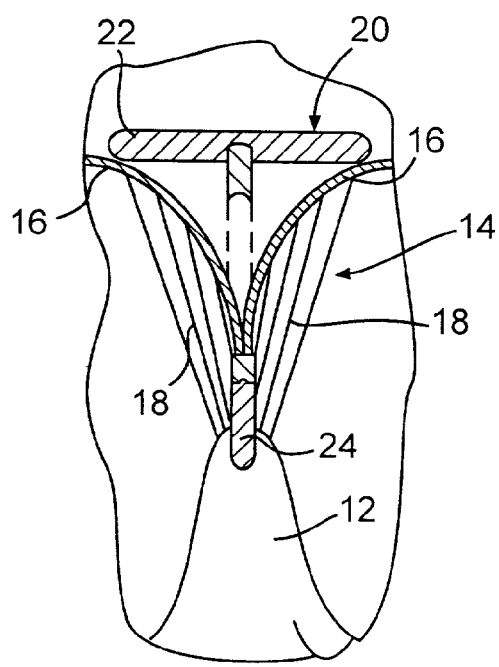
FIG. 6 is a cross section of a repaired valve and device in accordance with the present invention.

FIG. 6 is a view of the mitral valve 14 of FIG. 5 which has been modified by placement of valve repair device 20 as shown. Suture ring 22 is sewn proximate the annulus of valve 14, as known to those skilled in the use of suture rings. The annulus of valve 14 can be decreased in size by drawing the annulus toward the suture ring by the sutures used to connect ring 22 to the valve. Drawing the annulus of valve 14 toward suture ring 22 will help to eliminate opening 26. Tension member 24 is then anchored to papillary muscle 12 such that papillary muscle 12 is drawn toward valve 14. Whether or not the suture ring alone is sufficient to eliminate opening 26, drawing papillary muscle 12 toward valve 14 will provide additional stress relief on leaflet 16 promoting complete closure of valve 14. Drawing papillary muscle 12 toward 14 also reduces heart wall stress and increases chamber efficiency as discussed previously.

Figure 7:
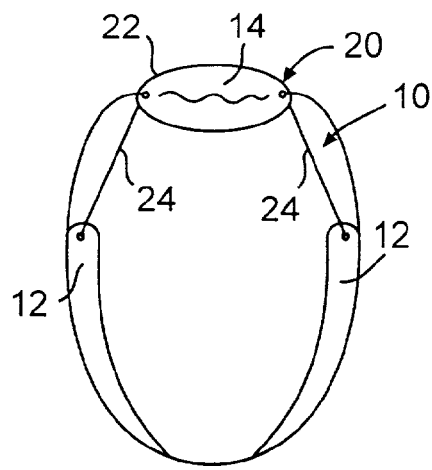
FIG. 7 is an embodiment of the device of the present invention.
Figure 8:
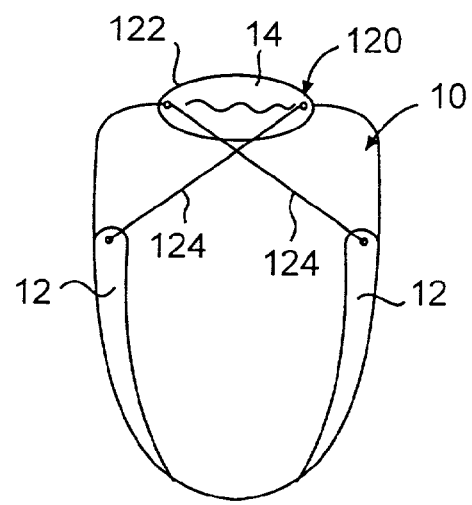
FIG. 8 is an alternate embodiment of a device in accordance with the present invention.

FIG. 7 is a highly simplified view of left ventricle 10 and valve repair device 20 as shown in FIG. 4. It can be noted that tension members 24 extend from basal anchor 22 to an adjacent papillary muscle 12. In contrast, FIG. 8 is a similar cross sectional view of left ventricle 10, but a valve repair device 120 is placed such that its tension members 124 extend between a basal anchor 122 and a papillary muscle 12 transversely opposite the point at which tension member 124 is connected to basal anchor 122. This arrangement, as opposed to that shown in FIG. 7, can increase the transverse component of the tension force in tension members 124 relative to the vertical component of that tensile force.

Figure 9:
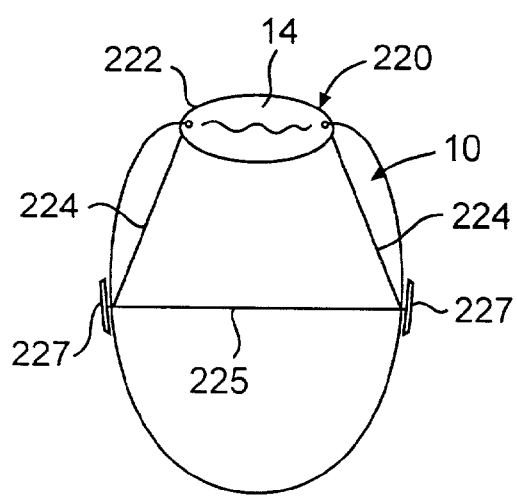
FIG. 9 is yet another alternate embodiment of a device in accordance with the present invention.

FIG. 9 shows yet another embodiment of the valve repair device in accordance with the present invention referred to by numeral 220. In this embodiment, device 220 is disposed in left ventricle 10 in a manner similar to that of device 20 shown in FIG. 7 in that tension members 224 of device 220 extend from a basal anchor 222 to an adjacent secondary anchor point. The secondary anchor point is established by transverse extension of a tension member 225 across left ventricle 10. Tension member 225 is anchored transmurally to the heart wall at its opposite ends by pads 227. In turn, tension members 224 are anchored or connected to tension member 225.

Tension member 225 can be used to further alter the geometry of left ventricle 10 in a manner disclosed in U.S. Pat. No. 5,961,440, entitled "HEART WALL TENSION REDUCTION APPARATUS AND METHOD", which was filed on Sep. 18, 1997 and is incorporated herein by reference.

Figure 10:
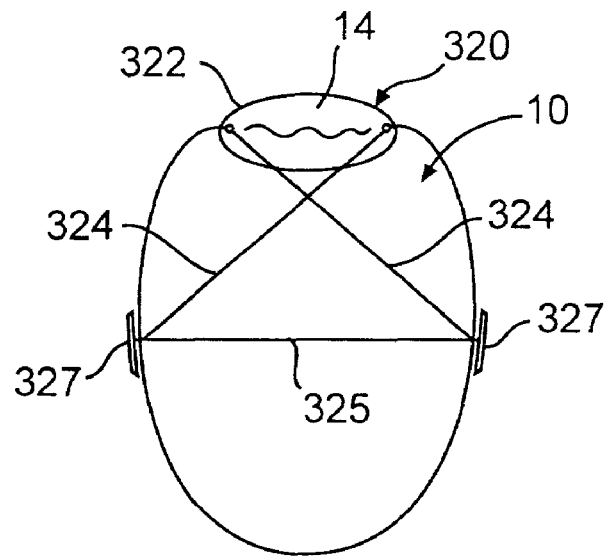
FIG. 10 is yet another alternate embodiment of the device in accordance with the present invention.

FIG. 10 shows yet another embodiment of a valve repair device in accordance with the present invention referred to by numeral 320. This embodiment includes a basal anchor 322 and tension members 324 and a transverse tension member 325 having anchor pads 327 similar to those of device 220. With respect to device 320, however, tension members 324 are crossed similar to those of device 120 of FIG. 8 to increase the horizontal component relative to the vertical component of the tensile force in tension member 324.

Figure 11:
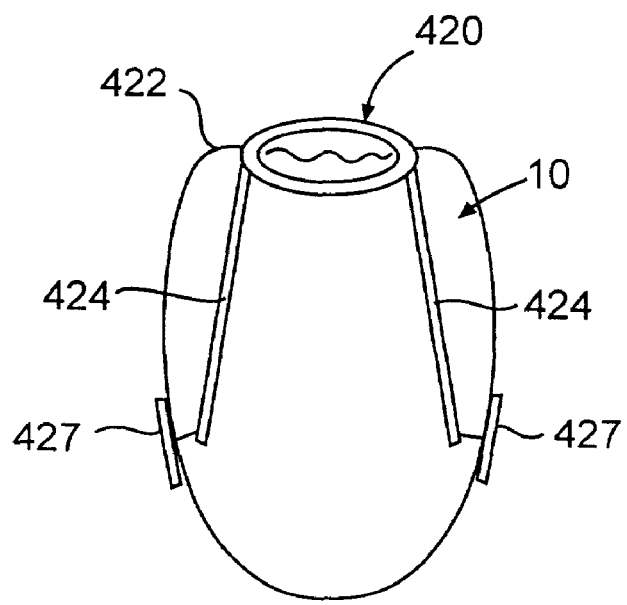
FIG. 11 is yet another alternate embodiment of a device in accordance with the present invention.

FIG. 11 is a yet another embodiment 420 of the valve repair device of the present method. Valve repair device 420 includes a basal anchor 422 and tension members 424. Tension members 424 are disposed in an arrangement similar to tension members 24 of device 20 shown in FIG. 7 except that tension members 424 are anchored transmurally by pads 427 rather than into papillary muscles 12. The relatively greater thickness of tension members 424 shown in FIG. 11, as compared to tension members 24 shown in FIG. 7, merely illustrates that the tension members can be substantially rigid or in the case of tension members 24, substantially flexible. It should be understood, however, that in any of the embodiments shown herein, the tension members could be advantageously formed to be substantially flexible or substantially rigid.

Figure 12:
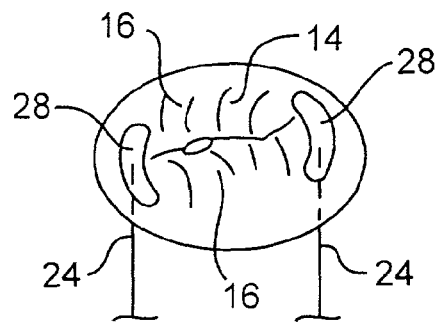
FIG. 12 is a view of a basal anchor for the device of the present invention.

FIG. 12 is a top or posterior view of valve 14. In this embodiment, the basal anchor for the valve repair device is shown as discrete pads 28 which can be sewn to the posterior side of valve 14. Tension members 24 are shown extending from respective pads 28 into the left ventricle.

Figure 13:
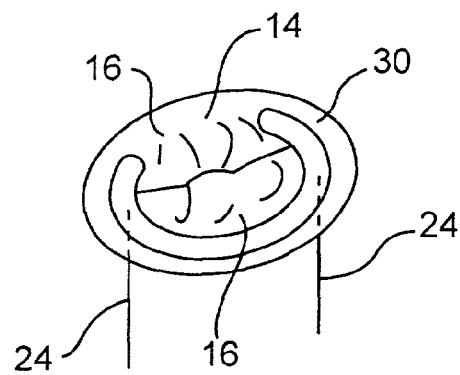
FIG. 13 is a suture ring serving as a basal anchor for the device of the present invention.

FIG. 13 is the same view of valve 14 as FIG. 12. In FIG. 13, however, the basal anchor 22 is shown as a crescent-shaped suture ring. Tension members 24 extends from basal anchor 22 through valve 14 into the left ventricle.

Figure 14:
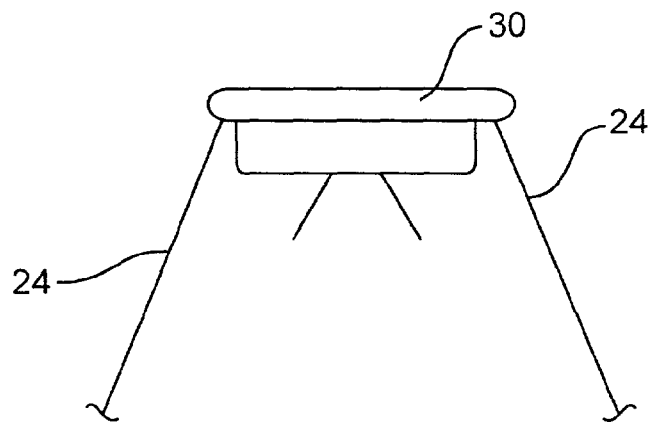
FIG. 14 is a replacement valve serving as a anchor for the device of the present invention.

FIG. 14 is a side view of an artificial heart valve 30. If it is necessary to replace the valve rather than merely repair it, artificial valve 30 can be used as a basal anchor for tension members 24.

Figure 15:
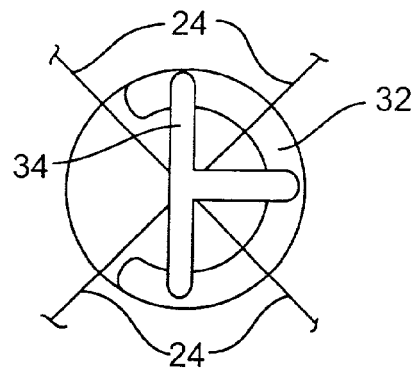
FIG. 15 is a top view of an alternate embodiment of a suture ring acting as an anchor for the device of the present invention.
Figure 16:
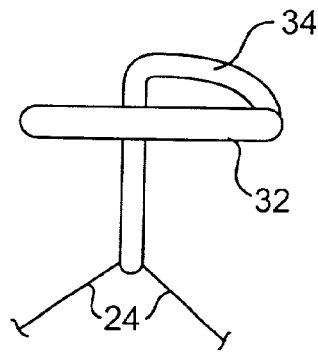
FIG. 16 is a side view of the suture ring of FIG. 15.

FIG. 15 is a top view of an alternate embodiment of a suture ring basal anchor 32. Ring 32 has a crescent shape and a pylon 34 extending through the mitral valve. FIG. 16 is a side view of suture ring 32 showing tension members 24 attached to pylon 34.

Tension members 24 preferably extend through the tissue of valve 14 rather than through the valve opening. It can be appreciated, however, that tension members 24 could be disposed through the valve opening. In the case of the embodiment of FIGS. 15 and 16, however, pylon 34 would be disposed through the valve opening. Tension members 24 associated with pylon 34 would be disposed on the opposite side of valve 14 from suture ring 32. Pylon 34 would preferably be disposed through the valve opening rather than the tissue forming valve 14.

Figure 17:
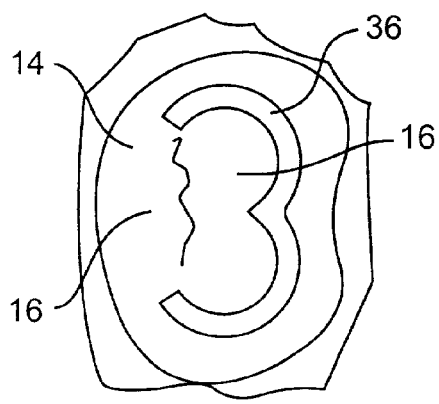
FIG. 17 is a view of an alternate embodiment of a suture ring which can act as basal anchor for the device of the present invention.
Figure 18:
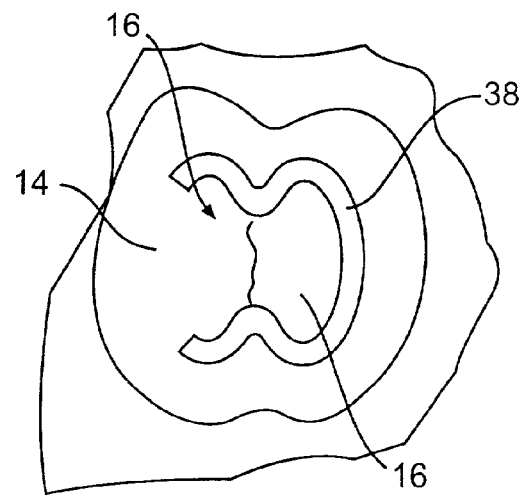
FIG. 18 is a view of yet another alternate embodiment of a suture ring which can act as a basal anchor for the present invention.

FIGS. 17 and 18 are yet additional alternate embodiments of suture rings which can be used as basal anchors in accordance with the present invention. The shape of the rings is selected such that as they are sewn into place on valve 14, the sutures can be used to draw tissue toward the inside of the ring, thus reducing the transverse and/or vertical cross sectional area of the associated heart chamber. This will advantageously reduce heart wall stress which is of particular benefit if the patient has a failing heart.

It can be appreciated that tension members 24 can be fixably or releasably attached to the basal anchor. Preferably, the tension members are fixably attached to the basal anchor during the valve repair procedure.

Figure 19:
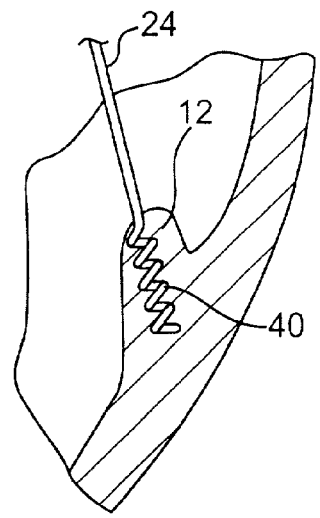
FIG. 19 is a embodiment of a secondary anchor for the device of the present invention.
Figure 20:
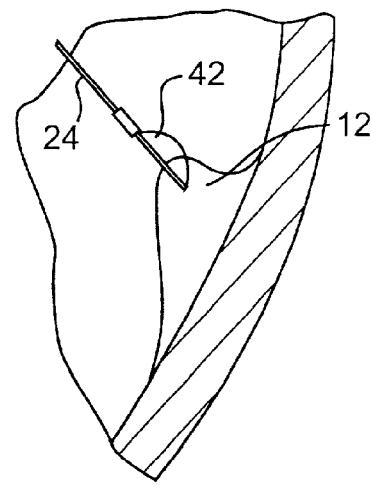
FIG. 20 is a view of an alternate embodiment of a secondary anchor for the device of the present invention.
Figure 21:
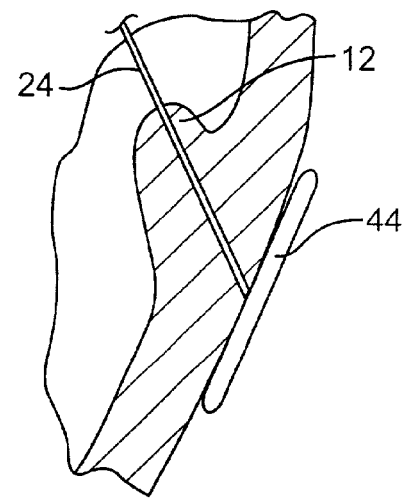
FIG. 21 is yet another embodiment of a secondary anchor for the device of the present invention.

FIGS. 19-21 show various configurations of anchoring devices shown at the second end of tension member 24. It can be appreciated that these anchoring devices could be used with each of the tension members described above. In FIG. 19, the second end of tension member 24 includes a secondary anchor 40 formed as screw which is shown augured into papillary muscle 12. FIG. 20 shows a secondary anchor 42 including a loop sewn through papillary muscle 12. FIG. 21 shows a tension member 24 extending transmurally to an exterior pad 44 to which it is connected. Tension member 24 could be sewn to pad 44 or otherwise mechanically connected thereto.

It can be appreciated that various biocompatible materials can be advantageously used to form the various components of the device of the present invention. It is anticipated that the present device will usually be chronically implanted. Thus, when selecting materials to form each of the components consideration should be given to the consequences of long term exposure of the device to tissue and tissue to the device.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method of passively treating an in situ mitral valve, the method comprising:
   securing a passive device to the in situ mitral valve, wherein the device includes a ring and a plurality of flexible elongate members extending therefrom into a left ventricle associated with the in situ mitral valve;
   extending a first flexible elongate member of the plurality of flexible elongate members from the ring across the ventricular cavity to a papillary muscle within the left ventricle;
   disposing a distal portion of the first flexible elongate member in direct contact with the papillary muscle;
   securing a first anchoring structure at the papillary muscle to a distal end of the first flexible elongate member so as to establish tension in the first flexible elongate member directly between the papillary muscle and the passive device;
   extending a second flexible elongate member of the plurality of flexible elongate members across the ventricular cavity directly to a second heart structure within the left ventricle other than a heart valve;
   securing a second anchoring structure at the second heart structure to a distal end of the second flexible elongate member so as to establish tension in the second flexible elongate member directly between the second heart structure and the passive device, wherein the second anchoring structure is discrete from the first anchoring structure.

2. The method of claim 1, further comprising drawing the papillary muscle toward the in situ mitral valve with the first flexible elongate member.

3. The method of claim 1, wherein securing the ring of the passive device to an atrial side of the in situ mitral valve includes drawing tissue towards an inside of the ring.

4. The method of claim 1, wherein the first and second flexible elongate members are fixably attached to the passive device.

5. The method of claim 1, wherein the first and second flexible elongate members are releasably attached to the passive device.

6. The method of claim 5, wherein the ring of the passive device is an annuloplasty ring.

7. The method of claim 1, wherein the ring of the passive device is an annuloplasty ring.

8. The method of claim 1, wherein the ring of the passive device is a suture ring.

9. The method of claim 1, wherein the second heart structure to which the second flexible elongate member extends is the heart wall.

10. The method of claim 1, wherein the second heart structure to which the second flexible elongate member extends is a second papillary muscle within the left ventricle.

11. The method of claim 10, wherein the flexible elongate members each extend from a point on the ring of the passive device across the ventricular cavity to an adjacent papillary muscle.

12. The method of claim 10, wherein the flexible elongate members each extend from a point on the ring of the passive device across the ventricular cavity to a transversely opposite papillary muscle.

13. The method of claim 1, wherein the first anchoring structure includes a transmural anchor pad.

14. The method of claim 1, wherein the first anchoring structure includes a hook-shaped papillary muscle tissue loop.

15. The method of claim 1, wherein the first anchoring structure includes a screw-shaped tissue anchor.

16. The method of claim 1, further comprising the step of placing a transverse flexible elongate member across the ventricular cavity and between the first and second anchoring structures so as to establish tension in the transverse flexible elongate member.

17. The method of claim 16, wherein the first and second anchoring structures include transmural anchors securing the opposite ends of the transverse flexible elongate member to the heart wall.

18. A method of passively treating an in situ mitral valve, the method comprising:
   securing a passive device to an atrial side of the in situ mitral valve, wherein the device includes a ring and a plurality of flexible elongate members;
   extending a first flexible elongate member of the plurality of flexible elongate members from the ring across the ventricular cavity to a first anchor point at a first papillary muscle within a left ventricle associated with the in situ mitral valve;
   disposing a first anchoring structure at the first anchor point to secure the distal end of the first flexible elongate member and so as to establish tension in the first flexible elongate member directly between the first papillary muscle and the passive device;

extending a second flexible elongate member of the plurality of flexible elongate members from the ring across the ventricular cavity to a second anchor point at a second papillary muscle within the left ventricle;

securing a second anchoring structure to the second anchor point to secure the distal end of the second flexible elongate member and so as to establish tension in the second flexible elongate member directly between the second papillary muscle and the passive device.

19. The method of claim 18, wherein securing the ring of the passive device to an atrial side of the in situ mitral valve includes drawing tissue towards an inside of the ring.

20. The method of claim 18, further comprising drawing the first papillary muscle toward the in situ mitral valve with the first flexible elongate member.

21. The method of claim 18, wherein the first and second flexible elongate members are fixably attached to the passive device.

22. The method of claim 18, wherein the first and second flexible elongate members are releasably attached to the passive device.

23. The method of claim 22, wherein the ring of the passive device is an annuloplasty ring.

24. The method of claim 18, wherein the ring of the passive device is an annuloplasty ring.

25. The method of claim 18, wherein the ring of the passive device is a suture ring.

26. The method of claim 18, wherein the flexible elongate members each extend from a point on the ring of the passive device across the ventricular cavity to an adjacent papillary muscle.

27. The method of claim 18, wherein the flexible elongate members each extend from a point on the ring of the passive device across the ventricular cavity to a transversely opposite papillary muscle.

28. The method of claim 18, wherein the first anchoring structure includes a transmural anchor pad.

29. The method of claim 18, wherein the first anchoring structure includes a hook-shaped papillary muscle tissue loop.

30. The method of claim 18, wherein the first anchoring structure includes a screw-shaped tissue anchor.

31. The method of claim 18, further comprising the step of placing a transverse flexible elongate member across the ventricular cavity and between the first and second anchor points so as to establish tension in the transverse flexible elongate member directly between the first and second papillary muscles.

32. The method of claim 31, wherein the first and second anchoring structures include transmural anchors securing the opposite ends of the transverse flexible elongate member to the heart wall, and the flexible elongate members are connected to the transverse flexible elongate member at the first and second anchor points.

* * * * *